United States Patent
Swor

[11] Patent Number: 5,364,375
[45] Date of Patent: Nov. 15, 1994

[54] CATHETER DEVICE FOR THE LOCALIZED INTRODUCTION AND MAINTENANCE OF PHARMACEUTICAL MATERIAL IN THE UTERINE CERVIX AND UPPER VAGINA

[75] Inventor: G. Michael Swor, Sarasota, Fla.

[73] Assignee: Surgical Safety Products, Inc., Sarasota, Fla.

[21] Appl. No.: 125,783

[22] Filed: Sep. 24, 1993

[51] Int. Cl.$^5$ .................. A61M 31/00; A61F 6/14
[52] U.S. Cl. ........................... 604/278; 128/841; 604/55
[58] Field of Search ............ 604/54, 55, 275–279, 604/284, 906; 128/834–841

[56] References Cited

U.S. PATENT DOCUMENTS

| | | | |
|---|---|---|---|
| 212,177 | 2/1879 | Berger | 604/278 |
| 650,080 | 5/1900 | Marmaduke | 604/278 |
| 1,566,061 | 12/1925 | Ziegler | 604/278 |
| 1,978,677 | 10/1934 | Kirk | 604/278 |
| 2,616,421 | 11/1952 | Greenberg | 604/278 |
| 2,764,975 | 10/1956 | Greenberg | 604/278 |
| 3,048,175 | 8/1962 | Uddenberg | 604/278 |
| 4,071,027 | 1/1978 | Meador | 604/55 |
| 4,100,923 | 7/1978 | Southern | 604/55 |
| 4,807,625 | 2/1989 | Singleton | 604/55 |
| 5,027,830 | 7/1991 | Koch | 128/841 |
| 5,104,377 | 4/1992 | Levine | 604/55 |
| 5,236,417 | 8/1993 | Wallis | 604/284 |

*Primary Examiner*—John D. Yasko
*Assistant Examiner*—Frank Wilkens, III
*Attorney, Agent, or Firm*—Allen, Dyer, Doppelt, Franjola & Milbrath

[57] ABSTRACT

A catheter device is described for the localized introduction of pharmaceutical material into the uterine cervix and the upper vagina. In one embodiment the catheter device comprises a flexible tube having a port at the proximal end and a rounded closed tip and an aperture away from the tip at the distal end. A diaphragm having a hole through which the tube may pass is used to seal off the cervix and upper vagina from the lower vagina, and a syringe is used to administer the pharmaceutical material through the port in the flexible tube. In a second embodiment two ports are provided in the flexible tube, enabling a flushing material to be ejected into the tube after the pharmaceutical material, thus ensuring that the entire dose of pharmaceutical material is delivered to the cervix and the upper vagina.

16 Claims, 2 Drawing Sheets

CATHETER DEVICE FOR THE LOCALIZED INTRODUCTION AND MAINTENANCE OF PHARMACEUTICAL MATERIAL IN THE UTERINE CERVIX AND UPPER VAGINA

FIELD OF THE INVENTION

The present invention relates generally to catheters useful in the female reproductive system, and more particularly for the introduction and maintenance of pharmaceutical material into the uterine cervix and upper vagina.

BACKGROUND OF THE INVENTION

Under certain medical and obstetrical circumstances, the uterine cervix of a woman at or near term does not undergo appropriate preparatory changes, and labor needs to be induced. It has been determined that a prostaglandin, known as prostaglandin E2, may be introduced endocervically to assist in ripening an unfavorable cervix.

The Upjohn Company has recently begun marketing a syringe prefilled with a premeasured single dose of 0.5 mg dinoprostone in 2.5 ml gel (Prepidil R Gel), administered through a catheter having a 10 or 20 mm shield near its distal end for blocking the cervix. The insertion of the catheter is accomplished with the use of a speculum to visualize the position of the cervix.

Atad (U.S. Pat. No. 4,976,692) discloses a catheter for use in the induction of labor that has two balloons positioned at the distal end of the catheter and an aperture in the catheter between the balloons. The catheter is positioned with the aid of a speculum so that the more distal balloon lies within the uterus and beyond the cervix and so that the more proximal balloon lies within the vagina proximal to the cervix. The more distal balloon is then inflated with fluid via one of three ports at the proximal end of the catheter, thus forming a blockage at the distal end of the cervix. The more proximal balloon is then inflated with fluid via the second of the three ports, thus sealing off the cervix from the vaginal side. Since the aperture in the catheter lies between the balloons, material may be introduced through the third port, which leads to the aperture, and the material is retained in the cervical area. A potential drawback to this apparatus is that the first balloon must reside within the uterus against the amniotic sac, thus raising the possibility of fetal harm. An economic disadvantage is that the apparatus has a complex construction, in that the catheter contains three ports, each opening onto one of three noncommunicating lumina.

SUMMARY OF THE INVENTION

The present invention comprises a catheter device for the introduction of material into a uterine cervix and/or the upper vagina. The material inserted can be introduced into the upper vagina or inner cervix as deemed appropriate by the operator. The catheter has two principal parts: a tubular member with a closed tip, an aperture near the tip, and a port through which the material to be administered is inserted; and a disk-shaped member, in one embodiment a diaphragm, having a hole approximately in its center through which the tubular member may pass. The disk has a periphery, in the case of a diaphragm a raised lip, that is capable of forming a liquid-impervious seal when placed in contact with the cervix.

In use the catheter device is inserted manually, that is, without the use of a speculum, the disk placed over the cervical opening by palpation, the plane of the disk being substantially perpendicular to the long axis of the vagina. The tubular member's tip, having been passed through the hole in the disk, may be positioned so that the aperture lies within the cervix, distal to the disk. Thus material emerging from the aperture is restrained from flowing back out of the upper vagina into the lower vagina.

A syringe can then be filled with any amount and composition of pharmaceutical material. After the tip of the syringe has been inserted into the port in the tubular member, the dose may be administered.

In another embodiment two ports are provided in the tubular member, both communicating with a common lumen. At least one of the ports is equipped with a removable closure. In this embodiment the same procedure already described is followed, with the second port blocked. Then this second port is opened, and another syringe containing flushing material is inserted into the second port. The flushing material is then ejected into the tubular member, serving to force the pharmaceutical material remaining in the lumen into the cervix. This process ensures that the desired dosage is delivered, that is, that the entire contents of the first syringe are actually delivered to the cervix.

It is thus an object of this invention to provide a catheter for the localized introduction of material into a uterine cervix.

It is a further object of the invention to maintain the placement of pharmaceutical material by means of a mechanical barrier.

It is another object of the invention to provide such a catheter device that may be inserted manually and thus avoid potential harm to a fetus or to the cervix.

It is yet a further object of the invention to provide such a catheter device that is capable of delivering a precise dosage of material.

Additional features of the present invention will become apparent with reference to the illustrations and the description to follow.

DETAILED DESCRIPTION OF THE PREFERRED EMBODIMENT

A description of the present invention will now be given with reference to FIGS. 1-4.

Single-Port Catheter Device

Figure 1:
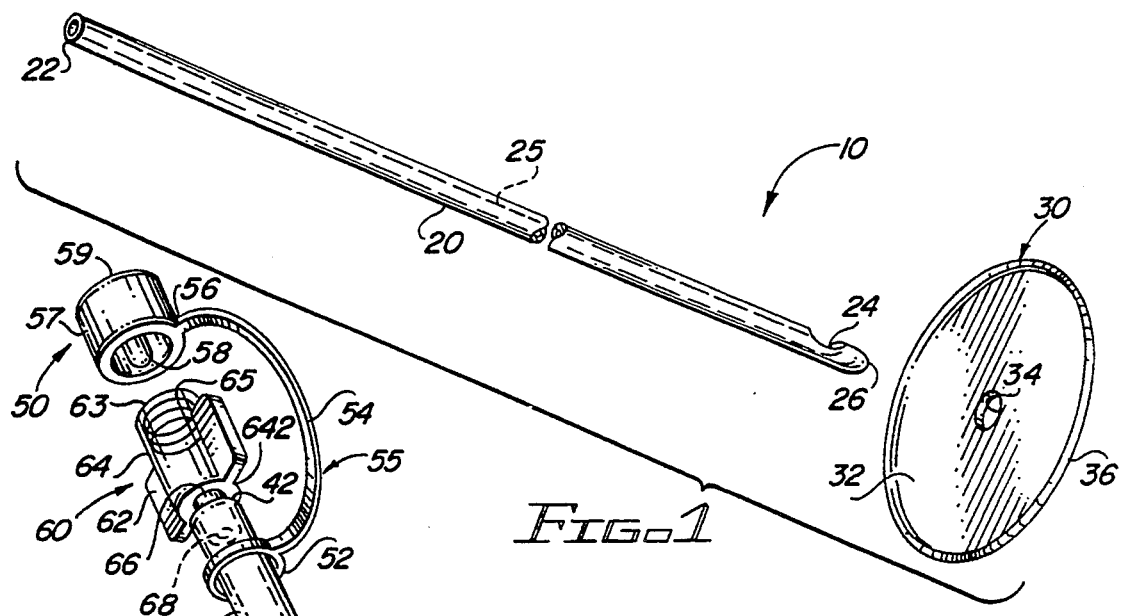
FIG. 1 illustrates the single-port catheter device assembly, including the tubular member and the diaphragm.
Figure 3:
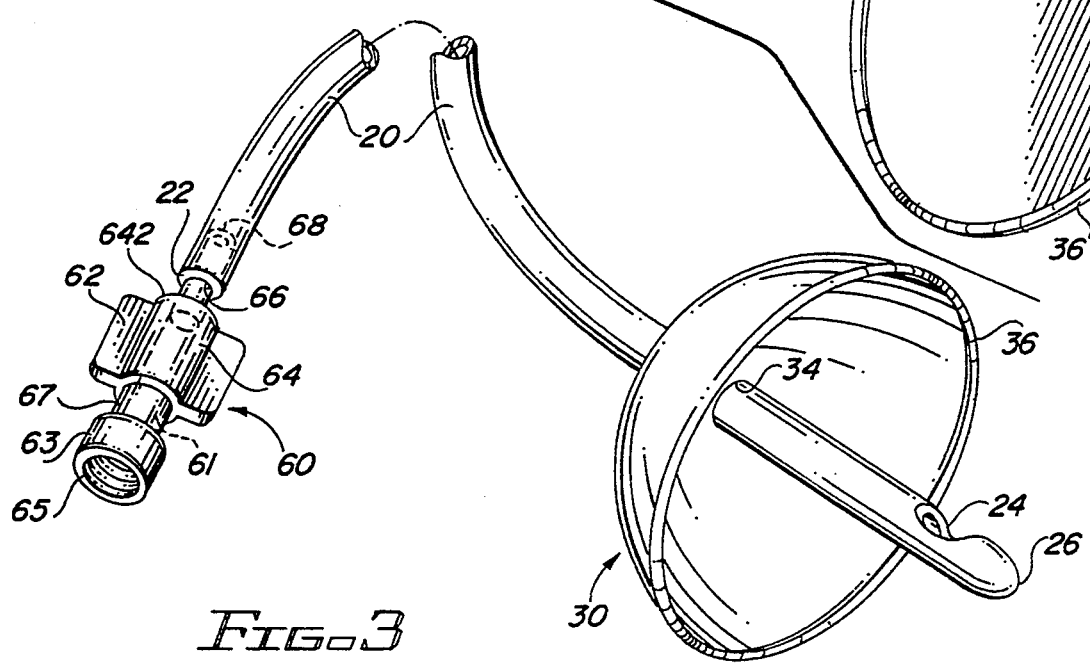
FIG. 3 shows the single-port catheter device assembled.

The single-port catheter device will be referred to generally by the reference numeral 10, as seen in FIGS. 1 and 3.

In the preferred embodiment the catheter device comprises a flexible tube 20 made of rubber, with an outer diameter of approximately 8 mm, an inner diameter of 3 mm, and a length of 25 cm. At the proximal end of tube 20 is port 22, in one embodiment capable of receiving the distal end of a syringe. Port 22 provides access to bore 25. At the distal end of tube 20 are closed, rounded tip 26 and aperture 24, which is proximal of tip 26 by approximately 1 cm. Aperture 24 has an elliptical shape, the major axis of the ellipse being parallel to the axis of tube 20. The major and minor axes are approximately 8 and 3 mm, respectively. The rounded shape of tip 26 facilitates its insertion, and the off-tip placement of aperture 24 mitigates against its becoming clogged during insertion.

In the preferred embodiment a coupling means, known as a Luer lock, is used for making the connection between the distal end of a syringe and the port 22 of tube 20, as is shown in FIG. 3. Luer lock 60 is an integrally molded rigid plastic member well known in the art. Luer lock 60 has a bore 61 therethrough and a cylindrical distal end 66 dimensioned to be inserted into port 22 of tube 20. Distal end 66 has an exit port 68. Central portion 64 of Luer lock 60 comprises a cylindrical portion 640 having a larger diameter than distal end 66. Shoulder 642 between distal end 66 and central portion 64 serves as a stop on the insertion of Luer lock 60 into port 22. Central portion 64 further comprises two wings 62 projecting radially outward at approximately 180 degrees from cylindrical portion 640. Wings 62 assist the user to grasp and manipulate Luer lock 60 upon insertion into port 22 and also in forming a connection with a syringe. Proximal to central portion 64 is cylindrical upper portion 67, having a diameter narrower than that of central portion 64. The proximal end of Luer lock 60 comprises lip 63 projecting out from upper portion 67 and threaded on its exterior for mating with a syringe. Luer lock port 65 in lip 63 provides the access to bore 66.

The catheter device further comprises a diaphragm 30 made of a flexible polymer such as Latex. Diaphragm 30 has a fairly rigid raised lip 36 dimensioned completely to surround the uterine cervix at the head of the vagina. Raised lip 36 also serves to form a liquid-impervious seal with the cervix.

Diaphragm 30 further comprises a flexible central portion 32 capable of forming a cuplike shape. Central portion 32 contains a circular hole 34 substantially in its center, dimensioned to permit tube 20 to pass therethrough and also to form a liquid-impervious seal. In the preferred embodiment, this hole is approximately 7 mm in diameter.

Figure 4:
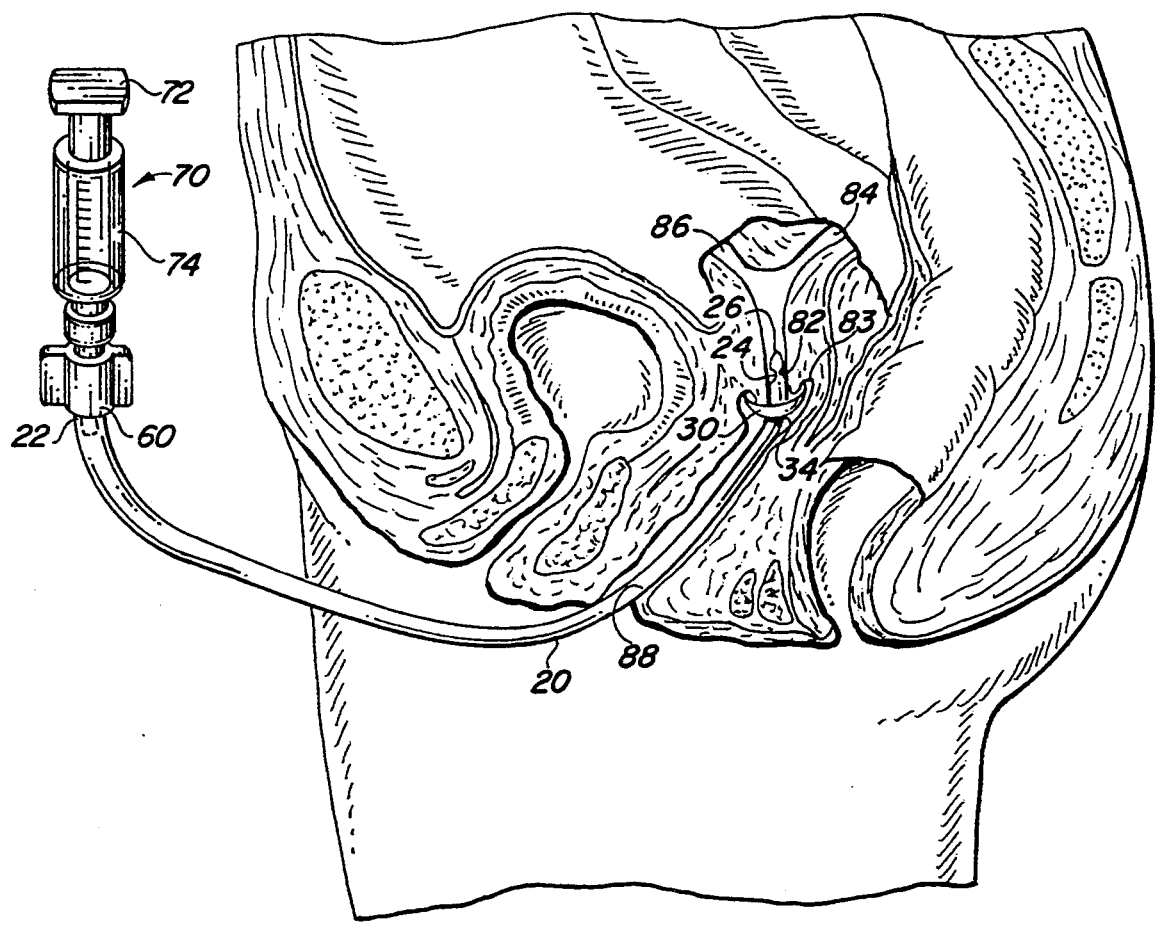
FIG. 4 illustrates the catheter device in position to deliver material to the cervix and/or the upper vagina.

The use of catheter device 10 will now be described with reference to FIG. 4. Diaphragm 30 is first inserted manually into the vaginal cavity 88 and placed against cervix 82, forming a liquid-impervious seal. Tube 20, having Luer lock 60 already attached to its proximal end, is then inserted manually, distal tip 26 first. Distal tip 26 is then passed through hole 34 in diaphragm 30 sufficiently far that aperture 24 resides completely in the cervix 82. The tip can, however, avoid the uterine space 84, and the amniotic sac 86. Syringe 70, its interior space 74 having been filled with a desired dosage of pharmaceutical product, in the embodiment considered here a prostaglandin gel preparation, is coupled with Luer lock 60. Syringe plunger 72 is depressed, causing the expulsion of gel through Luer lock bore 61, into tube bore 25, and out tube aperture 24. The gel thus enters cervix 82 and upper vagina 83 and is prevented from leaking from the upper vagina 83 into lower vagina 88 by diaphragm 30. The catheter device is retained in place for a specified amount of time and then removed.

Dual-Port Catheter Device

Figure 2:
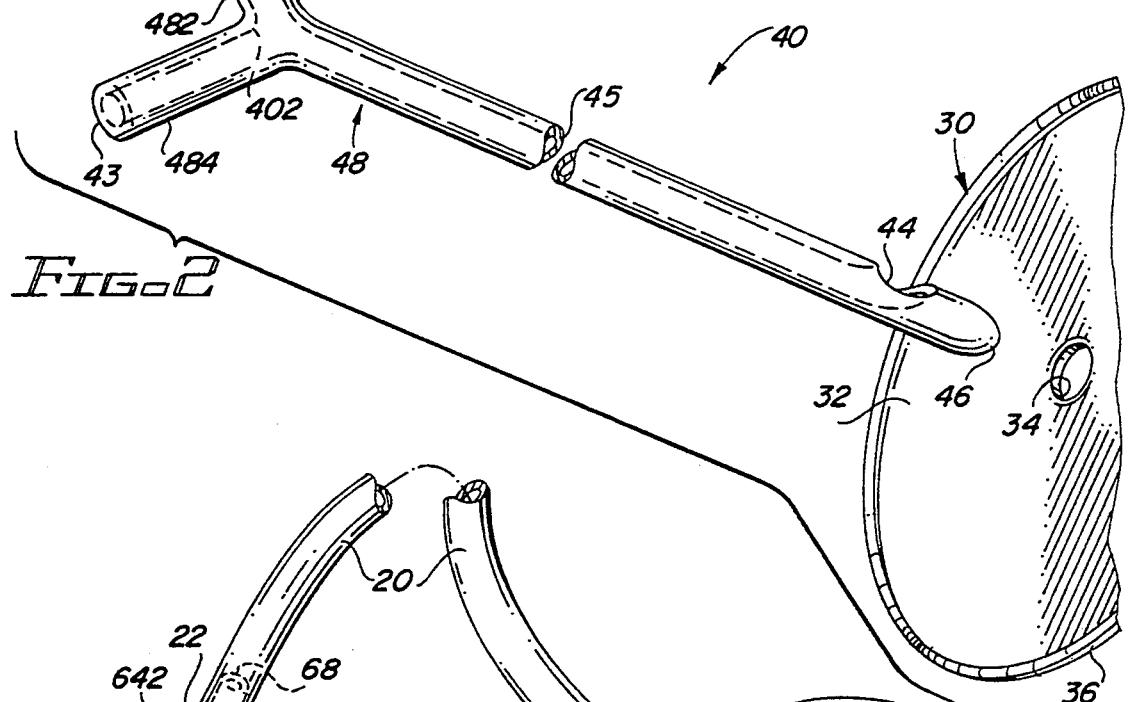
FIG. 2 depicts the two-port embodiment, also showing the closure mechanism attached to one of the ports.

The dual-port catheter device, referred to generally by the numeral 40, will be described with reference to FIG. 2.

In this embodiment diaphragm 30 is the same as that described for the single-port catheter device discussed above. The flexible tube 48 similarly comprises rounded tip 46 and aperture 44 at the distal end. At the proximal end, however, tube 48 splits into a "Y" junction 402, dividing tube 48 into two branches 482 and 484, providing two ports 42 and 43, both communicating with tube bore 45.

In the preferred embodiment at least one of the ports 42 or 43 is equipped with coupling means to provide a connection between a port and a syringe. This coupling means, as discussed in the single-port embodiment, comprises a Luer lock 60. As will be made clear in the description, during dual-port operation at least one of the ports 42 or 43 must be blocked. Therefore, at least one port closure means is needed, which is shown in FIG. 2 as cap 50.

Cap assembly 50, an integrally molded plastic member, comprises cylindrically shaped cover 56 and a guard assembly 55. Cover 56, which has a wall 57 having a serrated outer surface to facilitate handling, has an inner diameter larger than Luer lock lip 63 so that it may be placed over the proximal end of Luer lock 60. Projecting from the inner surface of the top 59 of cover 56 is plug 58, having an outer diameter smaller than the inner diameter of Luer lock port 65 so that when cover 56 is placed over the proximal end of Luer lock 60, plug 58 fits snugly inside port 65 and cover wall 57 fits snugly over lip 63.

Guard assembly 55 comprises guard ring 52 and attachment band 54. Attachment band 54, a thin flexible member, is attached at its proximal end to the top 59 of cover 56 and at its distal end to guard ring 52. Guard ring 52 is a torus dimensioned to fit loosely about tube 48 but sufficiently small that it cannot slide past shoulder 642. Assembly consists in placing guard ring 52 about one branch 482 of "Y" junction 402 in tube 48 and then inserting Luer lock 60 into tube port 42, thus retaining guard ring 52 between "Y" junction 402 in tube 48 and Luer lock 60. Therefore, whether cover 57 is engaged with Luer lock 60 or not, cap assembly 50 will remain with catheter 40.

The use of dual-port catheter device enables the delivery of a precise amount of pharmaceutical material to the cervix and the upper vagina. The first part of the procedure is identical with that described for the single-port embodiment, with the first port being used to deliver pharmaceutical material from a first syringe and the second port being blocked by a cap assembly. Following the administration of pharmaceutical material, the second port is unblocked, and a second syringe filled with a flushing solution, such as a saline or sterile gel, is attached to the Luer lock coupled to the second port, and the flushing solution is ejected. This flushing operation serves to thrust whatever pharmaceutical material remains in the bore 45 of tube 48 ahead of the flushing material, thereby delivering the precise amount of pharmaceutical material to the cervix and upper vagina.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A catheter device for the localized introduction of labor-inducing material into a uterine cervix and an upper vagina, the device comprising:

a tubular member having a distal end and a proximal end, the distal end having a closed tip and an aperture proximal to the tip, the proximal end having a port into which a material to be introduced into a uterine cervix and an upper vagina may be inserted, the tubular member further having a diameter dimensioned to pass easily into a human vagina having a long axis; and a disk, comprising:
   a central portion; and
   a periphery capable of forming a liquid-impervious seal with a uterine cervix;

the disk having a diameter dimensioned to fit inside the vagina such that the long axis of the vagina is substantially perpendicular to the plane of the disk;

the disk further having a hole substantially in the center of the disk, dimensioned to enable the distal end of the tubular member to pass therethrough and form a connection sufficiently tight to retain the material to be introduced into the uterine cervix and the upper vagina in a leakproof manner.

2. The catheter device recited in claim 1, wherein the disk is formed of a flexible material.

3. The catheter device recited in claim 2, wherein the periphery of the disk further comprises a raised lip.

4. The catheter device recited in claim 3, wherein the lip has less flexibility than the central portion.

5. The catheter device recited in claim 4, wherein the tubular member is formed of a flexible material.

6. The catheter device recited in claim 1, wherein the proximal end of the tubular member further comprises a second port into which a second material to be introduced may be inserted.

7. The catheter device recited in claim 6, wherein the proximal end further comprises means for closing at least one of the ports.

8. A catheter device for the localized introduction of labor-inducing material into a uterine cervix and an upper vagina, comprising:

a tubular member having a distal end and a proximal end, the distal end having a closed tip and an aperture proximal to the tip, the proximal end having a port into which a material to be introduced into a uterine cervix and an upper vagina may be inserted, the tubular member further having a diameter dimensioned to pass easily into a human vagina having a long axis; and a cup-shaped diaphragm, comprising:
   a central portion; and
   a substantially rigid raised lip around the circumference of the central portion, the lip being capable of forming a liquid-impervious seal with a uterine cervix;

the diaphragm having a diameter dimensioned to fit inside the vagina such that the long axis of the vagina is substantially perpendicular to an imaginary plane formed by the lip;

the diaphragm further having a hole substantially in the center, dimensioned to enable the distal end of the tubular member to pass therethrough and form a connection sufficiently tight to retain the material to be introduced into the uterine cervix and upper vagina in a leakproof manner.

9. The catheter device recited in claim 8, wherein the tubular member is formed of a flexible material.

10. The catheter device recited in claim 9, wherein the proximal end of the tubular member further has a second port into which a second material to be introduced may be inserted.

11. The catheter device recited in claim 10, wherein the proximal end of the tubular member further comprises means for closing at least one of the ports.

12. An applicator system for the localized introduction of labor-inducing material into a uterine cervix and an upper vagina, comprising:

a syringe having a distal end and an interior space dimensioned to hold the material to be introduced; and a catheter device, comprising:
   a tubular member having a distal end and a proximal end, the distal end having a closed tip and an aperture proximal to the tip, the proximal end having a port dimensioned to receive the distal end of the syringe, the tubular member further having a diameter dimensioned to pass easily into a human vagina having a long axis; and a cup-shaped diaphragm, comprising:
   a central portion; and
   a substantially rigid raised lip around the circumference of the central portion, the lip being capable of forming a liquid-impervious seal with a uterine cervix;

the diaphragm having a diameter dimensioned to fit inside the vagina such that the long axis of the vagina is substantially perpendicular to an imaginary plane formed by the lip;

the diaphragm further having a hole substantially in the center, dimensioned to enable the distal end of the tubular member to pass therethrough and form a connection sufficiently tight to retain the material to be introduced into the uterine cervix and upper vagina in a leakproof manner.

13. The applicator system recited in claim 12, further comprising:

a second syringe having a distal end and an interior space dimensioned to hold a second material to be introduced; and wherein the proximal end of the tubular member further has a second port dimensioned to receive and couplable to the distal end of the second syringe.

14. The applicator system recited in claim 13, further comprising means for reversibly closing at least one of the ports.

15. A method for introducing and localizing labor-inducing material into a uterine cervix and an upper vagina, comprising the steps of:

providing a cup-shaped diaphragm, comprising:
   a central flexible portion having a hole; and a substantially rigid raised lip around the circumference of the central portion, the lip being capable of forming a liquid-impervious seal with a uterine cervix;

placing the diaphragm against the cervix and forming a liquid-impervious seal between the lip and the cervix;

providing a syringe having a distal end and an interior space dimensioned to hold a material to be introduced into the uterine cervix and upper vagina;

providing a tubular member having a distal end and a proximal end, the distal end having a closed tip and an aperture proximal to the tip, the proximal end having a port dimensioned to receive the distal end of the syringe, the tubular member further having a diameter dimensioned to pass easily into a human vagina and that may be inserted manually;

inserting the distal end of the tubular member into the vagina and through the hole in the diaphragm sufficiently far that the aperture at the distal end passes completely through the hole in the diaphragm;

filling the interior space of the syringe with the material to be introduced;

inserting the distal end of the syringe into the port in the proximal end of the tubular member; and ejecting the material from the syringe into the tubular member, the material thereby proceeding through the tubular member and exiting the aperture at the distal end of the tubular member into the uterine cervix and the upper vagina.

16. A method for introducing and localizing a precise quantity of labor-inducing pharmaceutical material into a uterine cervix and an upper vagina, comprising the steps of:

providing a cup-shaped diaphragm, comprising:
a central flexible portion having a hole; and
a substantially rigid raised lip around the circumference of the central portion, the lip being capable of forming a liquid-impervious seal with a uterine cervix;

placing the diaphragm against the cervix and forming a liquid-impervious seal between the lip and the cervix;

providing a first syringe and a second syringe, each having a distal end and an interior space, the interior space of the first syringe dimensioned to hold a pharmaceutical material to be introduced and the interior space of the second syringe dimensioned to hold a flushing material;

providing a tubular member having a distal end and a proximal end, the distal end having a closed tip and an aperture proximal to the tip, the proximal end having a first port dimensioned to receive the distal end of the first syringe and a second port dimensioned to receive the distal end of the second syringe, the tubular member further having a diameter dimensioned to pass easily into a human vagina;

inserting the distal end of the tubular member into the vagina and through the hole in the diaphragm sufficiently far that the aperture at the distal end passes completely through the hole in the diaphragm;

filling the interior space of the first syringe with the pharmaceutical material to be introduced;

inserting the distal end of the first syringe into the first port in the proximal end of the tubular member;

blocking the second port in the proximal end of the tubular member;

ejecting the pharmaceutical material from the first syringe into the tubular member, the material thereby proceeding through the tubular member and exiting the aperture at the distal end of the tubular member into the uterine cervix and the upper vagina;

filling the interior space of the second syringe with the flushing material to be introduced;

opening the second port in the proximal end of the tubular member;

inserting the distal end of the second syringe into the second port in the proximal end of the tubular member; and ejecting the flushing material from the second syringe into the tubular member, the flushing material thereby thrusting the pharmaceutical material remaining in the tubular member in the proximal direction and out the aperture at the distal end of the tubular member into the uterine cervix and the upper vagina.

* * * * *